United States Patent [19]

Pohl et al.

[11] Patent Number: 4,999,098

[45] Date of Patent: Mar. 12, 1991

[54] MODIFIED MEMBRANE SUPPRESSOR AND METHOD FOR USE

[75] Inventors: Christopher Pohl, Union City; Roseanne W. Slingsby, Pleasanton; John R. Stillian, Livermore; Ryszard Gajek, San Francisco, all of Calif.

[73] Assignee: Dionex Corporation, Sunnyvale, Calif.

[21] Appl. No.: 837,330

[22] Filed: Mar. 3, 1986
(Under 37 CFR 1.47)

Related U.S. Application Data

[63] Continuation of Ser. No. 658,148, Oct. 4, 1984, abandoned.

[51] Int. Cl.$^5$ ............................................. B01D 61/48
[52] U.S. Cl. .................................. 204/301; 214/182.4
[58] Field of Search ................. 204/301, 182.4, 182.6, 204/182.3, 182, 182.5; 210/635, 638, 644, 656, 321.2, 294, 541, 198.2, 659; 422/70; 436/161, 175, 150, 100

[56] References Cited

U.S. PATENT DOCUMENTS

| | | | |
|---|---|---|---|
| 2,502,614 | 4/1950 | Zender | 210/321.2 |
| 2,784,158 | 3/1957 | Bodamer et al. | 210/321.2 |
| 2,799,644 | 7/1957 | Kollsman | 204/182.5 X |
| 3,046,211 | 7/1962 | Tye | 204/301 |
| 3,496,091 | 2/1970 | McGriff et al. | 204/301 |
| 3,761,386 | 9/1973 | Smith | 204/301 |
| 3,896,015 | 7/1975 | McRae | 204/301 |
| 4,265,634 | 5/1981 | Pohl | 210/656 |
| 4,303,493 | 12/1981 | Kneifel et al. | 204/301 |
| 4,337,141 | 6/1982 | Watanabe et al. | 204/301 |
| 4,403,039 | 9/1983 | Ban et al. | 210/656 |
| 4,455,233 | 6/1984 | Pohl et al. | 210/656 |
| 4,465,573 | 8/1984 | O'Hare | 204/301 |
| 4,529,521 | 7/1985 | Cortes et al. | 210/644 |
| 4,533,518 | 8/1985 | Hanaoka et al. | 422/70 |

FOREIGN PATENT DOCUMENTS

| | | | |
|---|---|---|---|
| 0032770 | 1/1981 | European Pat. Off. | |
| 0075371 | 9/1982 | European Pat. Off. | |
| 57-69251 | 4/1982 | Japan | 436/161 |
| 8200773 | 3/1982 | PCT Int'l Appl. | 422/70 |
| 1289738 | 9/1972 | United Kingdom | 204/301 |

OTHER PUBLICATIONS

Desalination, 19 (1976) 465-470, Elsevier Scientific Publishing Amsterdam, The Netherlands.

Primary Examiner—John F. Niebling
Assistant Examiner—John S. Starsiak, Jr.
Attorney, Agent, or Firm—Flehr, Hohbach, Test, Albritton & Herbert

[57] ABSTRACT

A suppressor for use in ion chromatography including at least an effluent flow channel separated by a charged membrane from a suppressor flow channel. A screen of the same charge as the membrane is placed in at least the effluent flow channel. Preferably, a similar screen is placed in the regenerant flow channel. The screen increases the dynamic capacity of the membrane suppressor.

22 Claims, 5 Drawing Sheets

FIG.—1

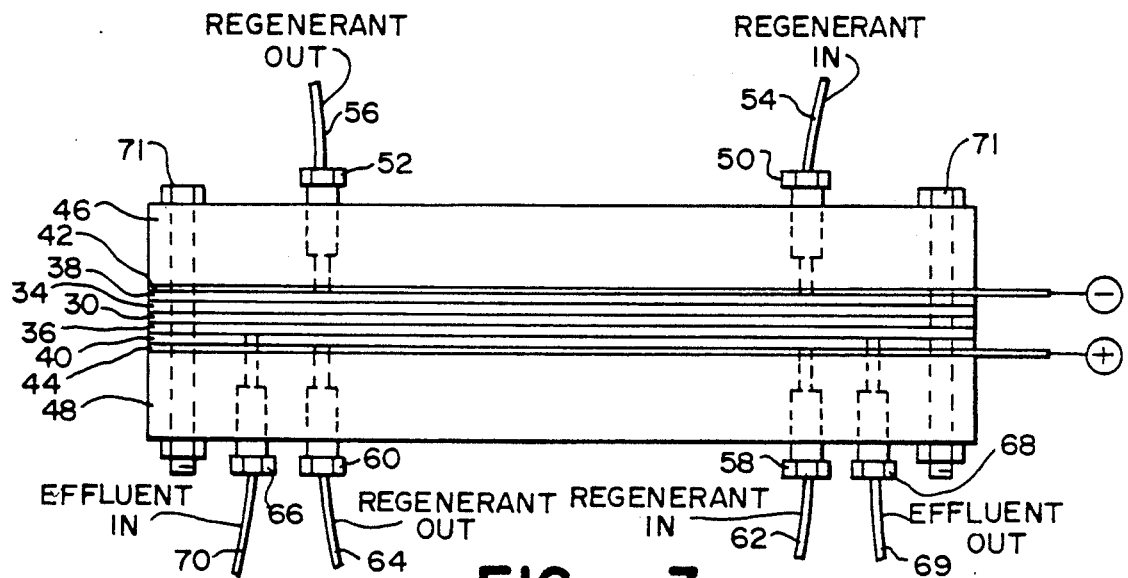
FIG.—3
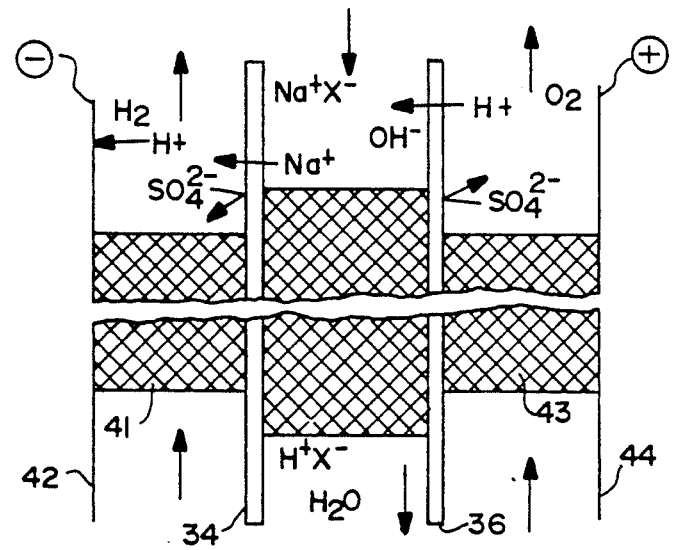
FIG.—4
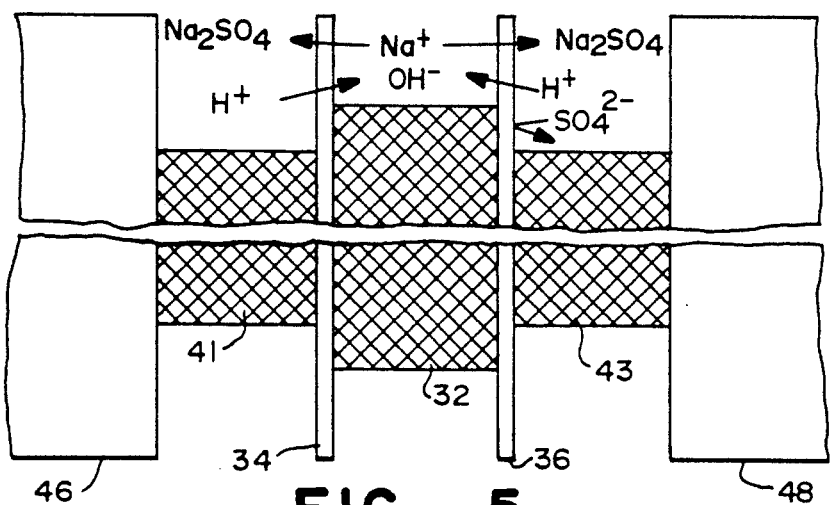
FIG.—5

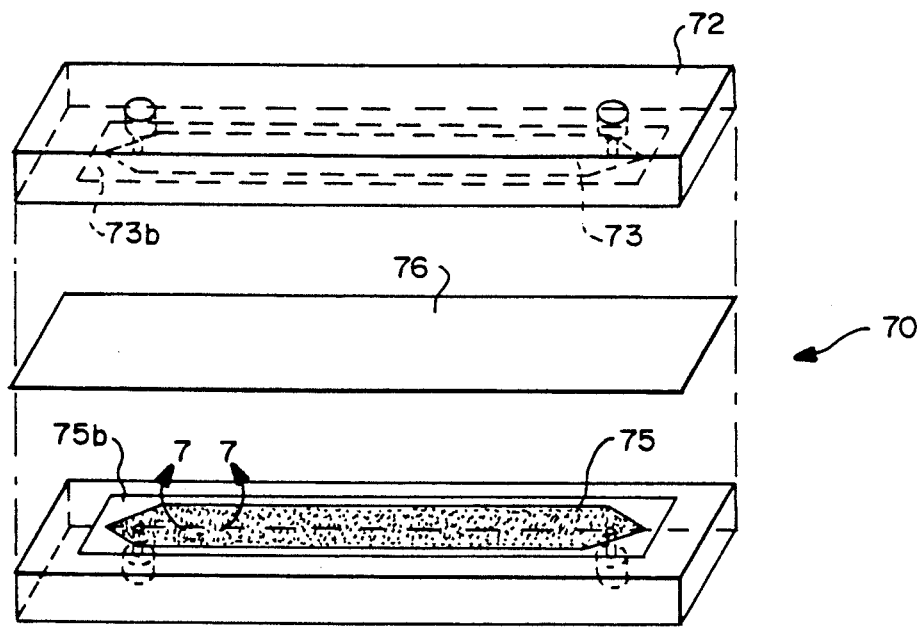
FIG.—6
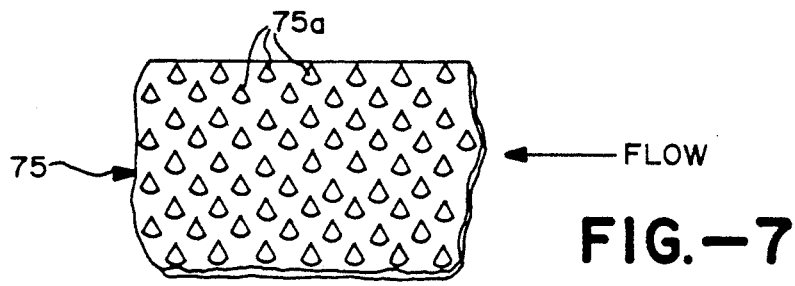
FIG.—7
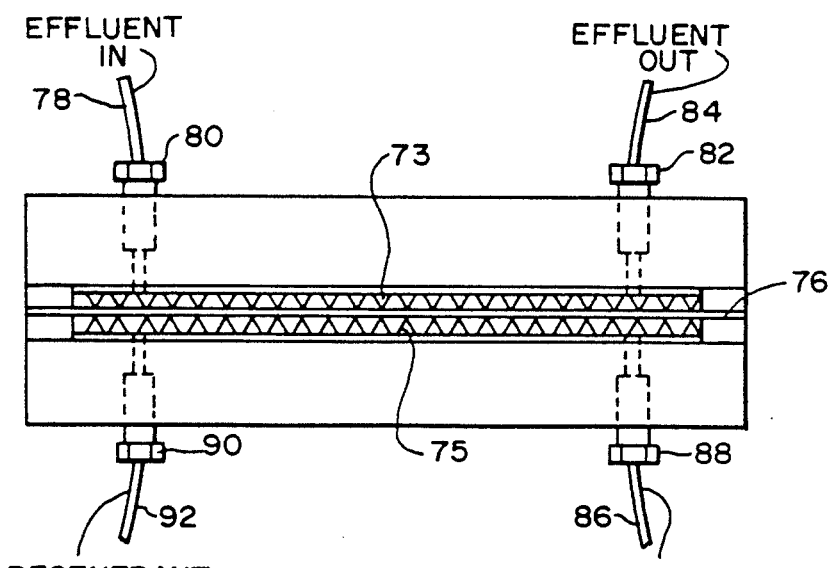
FIG.—8

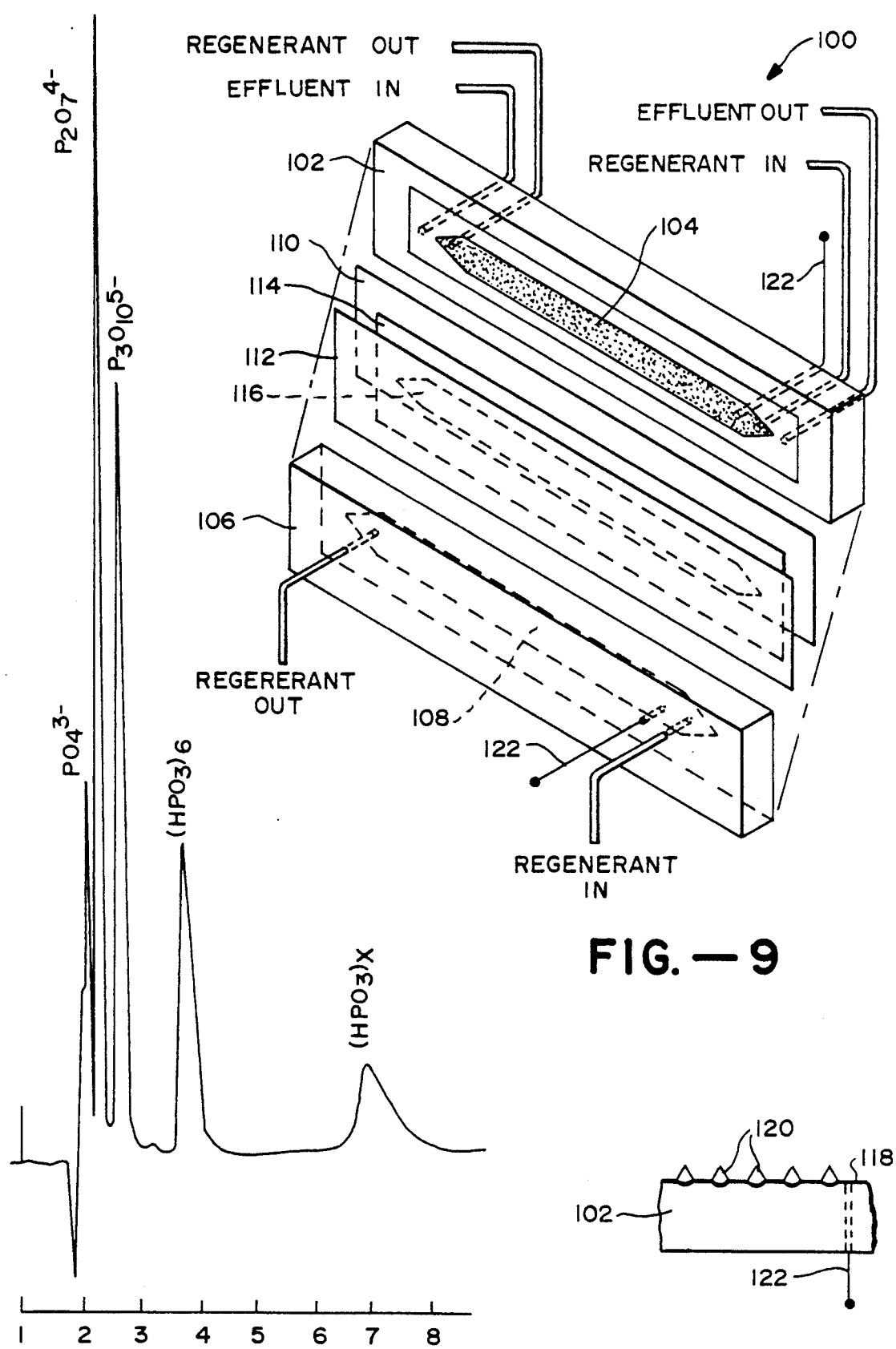
FIG.—9
FIG.—11
FIG.—10

MODIFIED MEMBRANE SUPPRESSOR AND METHOD FOR USE

This is a continuation of application Ser. No. 658,148 filed Oct. 4, 1984, now abandoned.

BACKGROUND OF THE INVENTION

The present invention relates to method and apparatus for the chemical suppression of eluents used in the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,956,559.

Suppression or stripping of the electrolyte is described in the above prior art references by an ion exchange resin bed. A different form of suppressor column is described and published in EPA Pub. No. 32,770, published July 29, 1981, in which a charged membrane in the form of a fiber or sheet is used in place of the resin bed. In sheet form, the sample and eluent are passed on one side of the sheet with a flowing regenerant on the other side of the sheet. The sheet comprises an ion exchange membrane partitioning the regenerant from the effluent of chromatographic separation. The membrane passes ions of the same charge as the exchangeable ions of the membrane to convert the electrolyte of the eluent to weakly ionized form, followed by detection of the ions.

An improved membrane suppressor device is disclosed in EPA Pub. No. 75,371, published Mar. 30, 1983. There, a hollow fiber suppressor is packed with polymer beads to reduce band spreading. There is a suggestion that such packing may be used with other membrane forms. Furthermore, there is a suggestion that the function of the fiber suppressor is improved by using ionically charged packing beads. No theory is set forth as to why such charged particles would function in an improved manner.

Another suppression system is disclosed in EPA Pub. No. 69,285, published Jan. 12, 1983. There, the effluent from a chromatographic column is passed through a flow channel defined by flat membranes on both sides of the channel. On the opposite sides of both membranes are channels through which the regenerant solutions are passed. As with the fiber suppressor, the flat membranes pass ions of the same charge as the exchangeable ions of the membrane. An electric field is passed between electrodes on opposite sides of the effluent channel to increase the mobility of the ion exchange. One problem with this electrodialytic membrane suppressor system is that very high voltages (50-500 volts DC) are required. As the liquid stream becomes deionized, electrical resistance increases, resulting in substantial heat production. Such heat is detrimental to effective detection because it greatly increases noise and decreases sensitivity.

Charged fiber screens have been suggested for placement in a flow channel between oppositely charged membranes in the field of electrodialysis to improve current efficiency for desalination. (*Desalination* 19 (1976) 465–470) The charges on individual fibers are either cationic or anionic so that only fibers of one charge contacts the correspondingly charged permselective membrane in a stack. There is no suggestion that such screen would have any applicability to an analytical system.

SUMMARY OF INVENTION

In accordance with the invention, apparatus and methods are provided for significantly improving the effectiveness of suppressing the electrolyte of the eluent in an effluent stream containing the separated ions removed from a separation column such as a chromatographic column. Referring to the apparatus, the suppressor includes at least one regenerant compartment and one effluent compartment separated by an ion exchange membrane sheet defining a regenerant flow channel and an effluent flow channel on opposite sides of the membrane sheet. The sheet is preferentially permeable to ions of the same charge as its exchangeable ions. Bridging means is disposed in at least the effluent flow channel in the form of structure including continuous portions extending substantially the entire distance between the membrane sheet and the effluent compartment wall. The structure defines a continuous convoluted liquid flow-through passage in the effluent flow channel. The external surfaces of the structure include all cation or all anion ion exchange sites. A detector, such as an electrical conductivity detector, is provided for detecting the resolved ionic species. The structure suitably comprises a screen with ion exchange sites and serves to provide site-to-site transfer paths across the effluent flow channel to significantly increase the suppression efficiency of the device. In another embodiment, the bridging means may comprise spaced projections along the effluent compartment wall extending towards the membrane, in the form of a textured wall or the like. Preferably, additional bridging means of similar type also is disposed in the regenerant channel. The bridging means also serves as a turbulence promoter in this system and contributes to the efficient use of the ion exchange membrane surface.

In another embodiment, termed a "sandwich suppressor", a second membrane sheet is included opposite to the first membrane sheet defining therebetween the effluent flow channel. A second regenerant compartment defining a flow-through channel is provided on the opposite side of the second membrane sheet from the effluent compartment. This further improves the capacity of the suppressor device.

Spaced electrodes may be provided in communication with each of the regenerant flow channels along the length of the sandwich suppressor. When an electrical potential is applied across the electrodes, there is an increase in mobility of the ions of interest across the membranes.

BRIEF DESCRIPTION OF THE DRAWINGS

FIG. 3 is a side view of a membrane suppressor illustrating effluent and regenerant flow channels in dotted lines.

FIGS. 4 and 5 are schematic expanded views of the membranes and screens showing simplified ion transfer in which an electrical potential is applied and not applied respectively.

FIG. 6 is an exploded view of a suppressor device including a single regenerant flow channel and bridging means in the form of a textured wall.

FIG. 7 is an enlarged portion of the textured wall, of FIG. 6 taken in the area 6—6 of FIG. 6.

FIG. 8 is an assembled cross-section view of the device of FIG. 6.

FIG. 9 is an exploded view of a sandwich suppressor device with regenerant textured walls and an effluent flow channel with a screen.

FIG. 10 is an expanded view of a section of the texture block of FIG. 9.

FIG. 11 is a chromatogram generated according to Example 3.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as $\mu$Eq./min of eluent for each device; (2) background conductivity measured as $\mu$S/cm per device, and (3) chromatographic efficiency measured as a width at half height for flow injection or 5.5 (retention time/width at half height)$^2$ for the species retained in a separator.

The term "efficiency" describes the chromatographic properties in terms of the maintenance of the narrowness of the analyte bands that elute from the separator. On the other hand, "capacity" describes in quantitative terms the concentration of eluent that can be suppressed per unit time.

Figure 1:
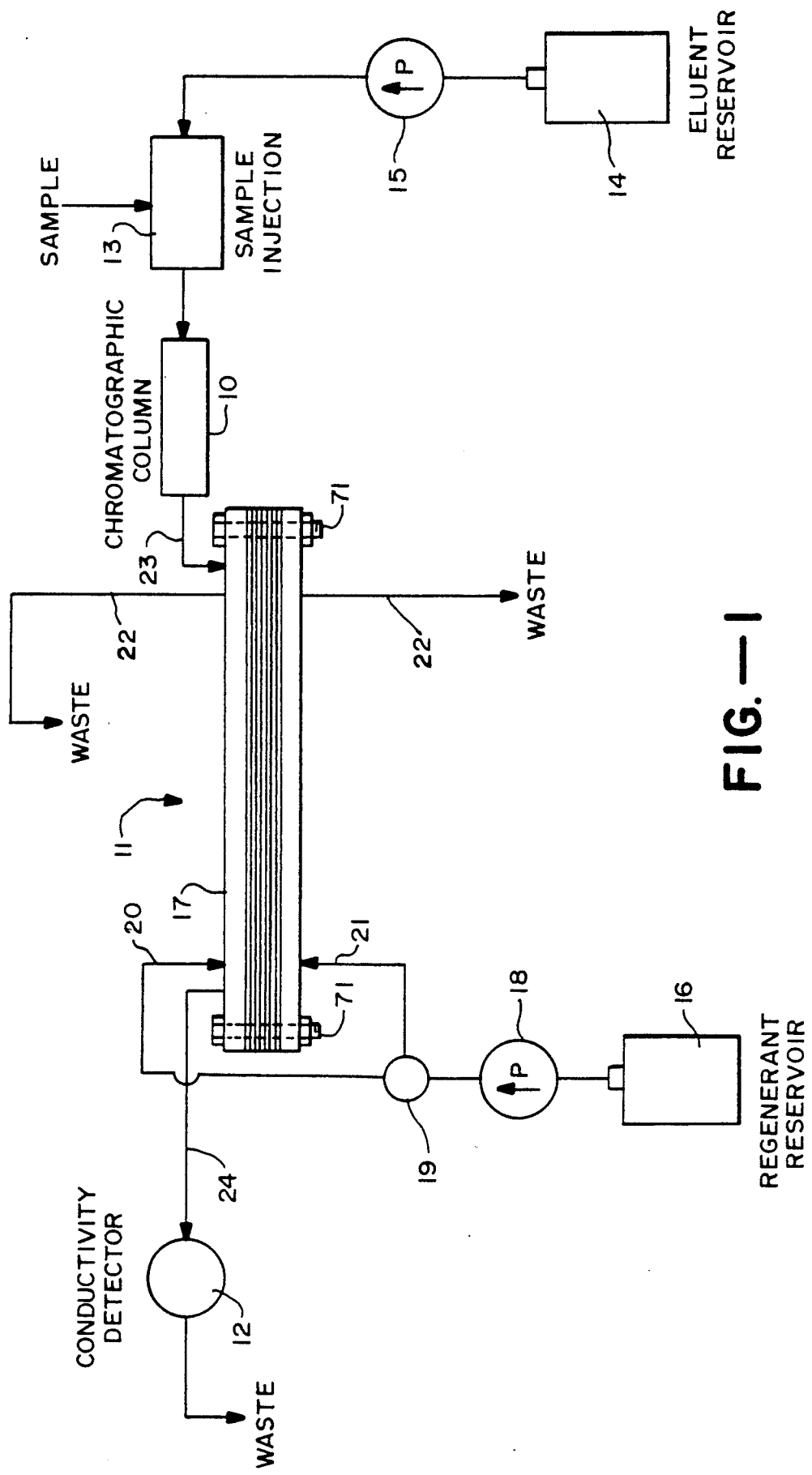
FIG. 1 is a schematic view of apparatus for performing ion chromatography in which the suppressor device of the present invention is used.

Referring to FIG. 1, a simplified apparatus for performing the present invention is illustrated. The system includes chromatographic separation means, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is suppressor means 11 serving to suppress the conductivity of the electrolyte of the eluent from column 10 but not the conductivity of the separated ions. The conductivity of the separated ions is usually enhanced in the suppression process.

The effluent from suppressor means 11 is directed to a detector in the form of conductivity cell 12 for detecting all the resolved ionic species therefrom, preferably in the form of a flow-through conductivity cell. A suitable sample is supplied through sample injection valve 13 which is passed through the apparatus in the solution of eluent from eluent reservoir 14 drawn by pump 15, and then pass through the sample injection valve 13. The solution leaving column 10 is directed to suppressor means 11 wherein the electrolyte is converted to a weakly conducting form. The effluent with separated ionic species is then treated by suppressor means 11 and pass through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

Suppressor means 11 includes a regenerant reservoir 16 or other source of regenerant solution which is directed to at least one flow-through regenerant channel in ion-exchange membrane device 17. The membrane device will be described in detail hereinafter. Regenerant from reservoir 16 flows through a chromatographic pump 18 and a splitter valve 19 which separates the regenerant into two different conduits 20 and 32 to supply the regenerant to the regenerant flow-through passages and then to waste through conduit 22. Alternatively, the regenerant flows through the regenerant chambers sequentially then to waste. The effluent flows from chromatographic column 10 to membrane device 17 through conduit 23, and from the membrane device to the conductivity detector through conduit 24.

Sandwich Suppressor Device

Referring to FIGS. 2-5, a device is illustrated in the form of a sandwich suppressor device including a central effluent flow channel defined on both sides by membranes to the exterior of which are two regenerant flow channels.

Figure 2:
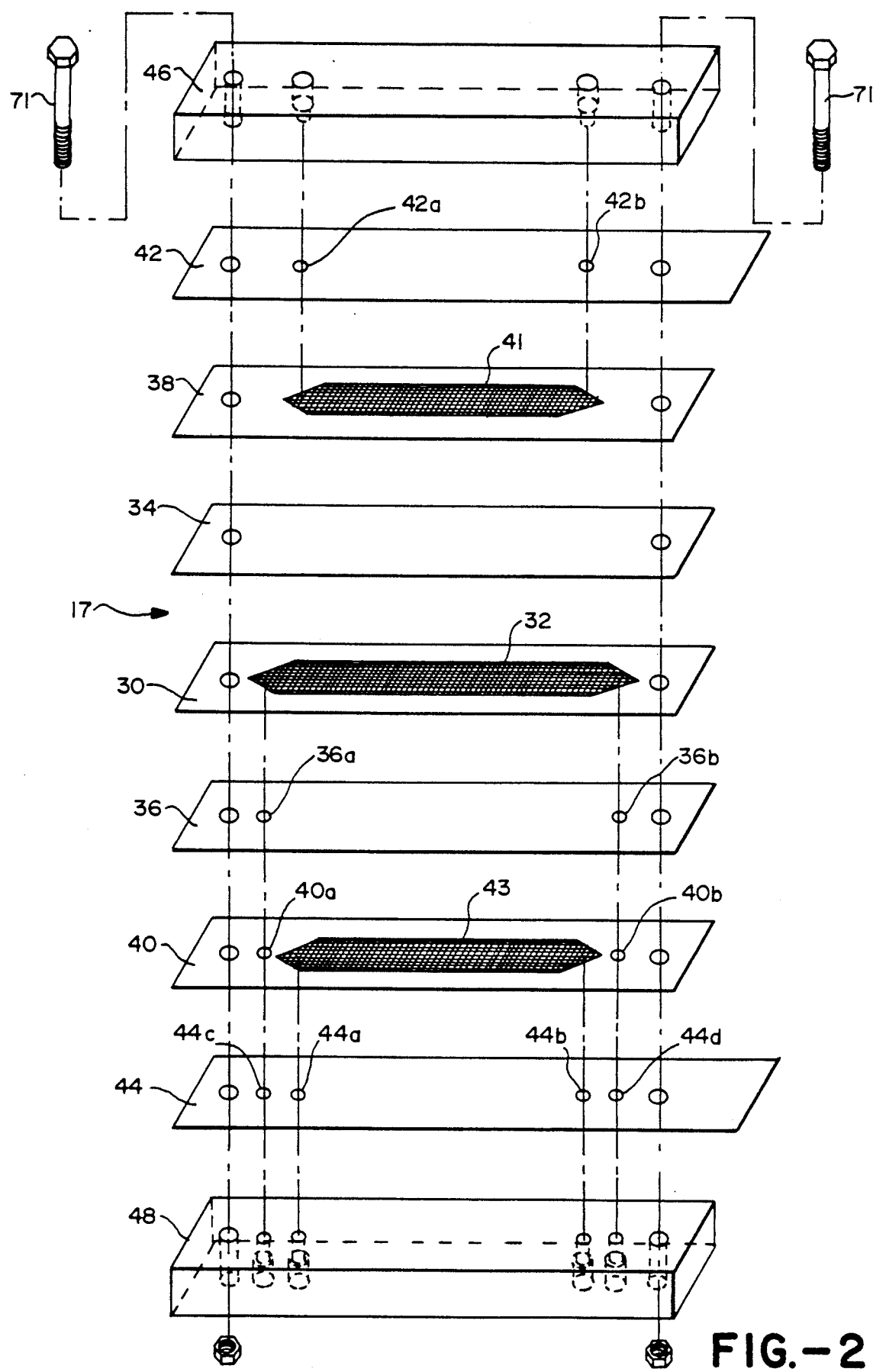
FIG. 2 is an exploded view of a suppressor device including two regenerant flow channels and a central effluent flow channel, each including a screen.

Referring specifically to FIGS. 2 and 3, membrane device 17 is illustrated which includes a central effluent flow channel flanked by regenerant flow chanels. Membrane device 17 includes means defining an effluent flow channel in the form of an effluent compartment, partially bounded by an effluent gasket 30 defining a central cavity. To minimize dead space in the cavity it is preferable to form both ends of the flow channels in a peak or V-shape. Bridging means is disposed suitably in the form of effluent screen 32, to be described more fully below. Membrane sheets 34 and 36 are mounted to extend along opposite sides of effluent screen 32 and, together with gasket 30, define the outer perimeter of the effluent flow channel. Openings 36a and 36b are provided for effluent inlet and outlet to the effluent flow channel.

Regenerant gaskets 38 and 40 are mounted to the facing surfaces of membrane sheets 34 and 36, respectively and define regenerant flow channels. Bridging means may be provided in the regenerant flow channels in the form of screens 41 and 43, respectively. Openings 40a are 40b are provided for inlet and outlet effluent flow through gasket 40. To simplify connections with the external flow lines, it is preferable to form the effluent flow channel slightly longer than the flanking regenerant flow channels.

As illustrated, flat plate electrodes 42 and 44 are mounted to the exterior sides of gaskets 38 and 40, respectively, across which an electrical potential is applied. Electrode 42 includes openings 42a and 42b to permit the inlet and outlet flow of regenerant solution to the regenerant flow channel in gasket 38. Similarly, electrode 44 includes inlet and outlet openings 44a and 44b, respectively, for regenerant liquid flow and to the regenerant flow channel and gasket 40, and also defines inlet and outlet openings 44c and 44d for the effluent flow channel defined by gasket 30.

External support blocks 46 and 48 are formed of a rigid nonconductive material, such as polymethylmethacrylate, and serves to provide structural support for the remainder of membrane device 17. Referring to FIG. 3, fittings 50 and 52 are provided for regenerant inlet and outlet lines 54 and 56, respectively. Similarly, fittings 58 and 60 are provided for regenerant inlet and outlet lines 62 and 64, respectively. Fittings 66 and 68 are provided for effluent inlet and outlet lines 70 and 69, respectively. The fittings may be mounted to the support blocks by any conventional means such as mating screw threads.

The above assembled sheets and gaskets are mounted under pressure supplied by bolts 71 to form liquid-tight seals. Also, by use of such pressure in combination with appropriate sizing of the screen (or other bridging means described below) in comparison to the flow channel dimensions, the screen extends substantially the entire distance across the flow channels and contacts the membranes, resulting in significantly improved ion transport and efficiency. It is preferable for maximum membrane transfer efficiency to connect the lines to the effluent and regenerant flow channels for countercurrent flow.

Effluent gasket 30 may be formed of any suitable material which provides a liquid seal for the effluent flow channel which it defines. A suitable material for the gasket is a flexible liquid silicone-based rubber such as supplied under the name RTV by General Electric Co. or a plastic sheet such as "Parafilm" supplied by American Can Co. A similar material may be used for regenerant gaskets 38 and 40.

Ion-exchange membrane sheets 34 and 36 may be of a type such as disclosed in Slingsby, et al. patent application, Ser. No. 522,828, filed Aug. 12, 1983. In particular, such sheets may be cation-exchange or anion-exchange membranes with polyethylene, polypropylene, polyethylenevinylacetate-based substrates. Other suitable substrates include poly-vinylchloride or polyfluorocarbon-based materials. The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alyklvinylpyridines. As an example, to form a cation-exchange membrane, the sheets grafted with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2-4 mil when wet. Suitable polyethylene substrate membranes of the foregoing type are provided by RAI Research Corp., Hauppauge, N.Y. (the cation-exchange membrane provided under designation R5010 (0.008 in. thick) and the anion-exchange membrane under designation R4015 (0.004 in. thick)). Other cation exchange membranes supplied by the same company which are fluorocarbon based include R1010 (0.002 inch thick) and R4010 (0.004 inch thick).

Bridging means, illustrated as effluent screen 32 in the embodiment of FIGS. 2 and 3, is a significant feature of the present invention and serves a number of important functions. Effluent screen 32 may be formed integral with effluent gasket 30 or may be inserted independently into the effluent flow channel.

A screen integral with the surrounding gasket material may be formed by cutting a gasket from plastic sheet to include the desired flow path and pressing this gasket into a rectangular piece of screen such that only the flow path is not covered by the gasketing material Regenerant screens 41 and 43 may be formed in the same manner as set forth with respect to effluent screen 32. The effluent bridging means includes continuous portions which extend substantially the entire distance across the effluent flow channel transverse to flow. In the embodiment of FIGS. 2 and 3, this distance extends between membrane sheets 34 and 36. In alternate embodiment of FIGS. 6-8 described below, only one membrane separates one regenerant flow channel from the effluent flow channel. There, the transverse distance spanned by the bridging means is from the membrane to the opposite wall defining the effluent flow channel. The bridging means defines a continuous convoluted flow-through passageway in the effluent flow channel along substantially the entire length of the membrane. This creates turbulence and thus increasing the efficiency of mixing and transfer of the ions across the membrane as described below. The physical configuration of the screen may vary so long as its bridging function and turbulence-producing function is accomplished. Thus, the screen may be provided with a weaving pattern either perpendicular or diagonal to the direction of flow. Also, the fibers may be smooth or contain protrusions such as bumps. The bridging means may also be in other forms, such as a textured block, as described below.

A major function of the bridging means is to provide a site-to-site path for ions in the direction transverse to the effluent flow channel to increase the efficiency of ionic transfer across the ion-exchange membrane as more fully described below. Bridging means in the form of a screen may be functionalized for this purpose in a manner analogous to the functionalization of the ion-exchange membranes set forth above. Suitable screens may be formed of the same base polymers grafted with the same functionalizing monomers as those set out above for the membranes.

The maximum chromatographic efficiency of the screen embodiment of the bridging means may be achieved using a relatively small mesh (measured after functionalization), e.g. on the order of 110μ mesh size or less with relatively thin fibers, e.g., on the order of 0.004 inch in diameter. An open area in the flow channel on the order of 5% to 70% (preferably, on the order of 8%) provides excellent efficiencies. A suitable proportion of grafting monomer to grafting polymer substrate is on the order of 5%–50% (preferably about 25% to 35%). In order to obtain maximum efficiency, the effluent flow channel should be fairly narrow, e.g., on the order of 0.5 cm, with the weave pattern oriented diagonally to the direction of flow.

To maximize the dynamic capacity of the regenerant screens they may be functionalized to relatively high ion exchange capacity, e.g. 2 meq/g. Also, as with chromatographic efficiency, it is preferable to orient the fibers of the screen diagonally to the direction of flow in the eluent and regenerant chambers. As the exposed membrane surface area increases suppression capacity increases. However, practical limits are prescribed by known principles of chromatography. For example, to minimize band broadening, a minimum volume is desired.

The following parameters are relevant to the screen's function; weave patterns, orientation of weave pattern to flow, ion exchange capacity, mesh, and percentage of open area relative to volume. The use of an ion exchange screen in a liquid flow path improves both dynamic suppression capacity and chromatographic efficiency. Several weaves may be used including twill, twill square, half-leno, dutch weave and, preferably, plain square weave. With plain square weave, the warp and weft threads are woven in a simple over and under pattern. The over and under pattern is preferred since it produces a turbulent path for liquid flow transversely as well as laterally and longitudinally. As set forth above, the square weave preferably is oriented approximately 45° to the direction of liquid flow causes the liquid to be dispersed to the outer walls of the gasketed chamber (covering more membrane surface) in a shorter time than in the case where the weave is oriented 90° to flow. Interplay is present between these parameters and the mesh since the product of the mesh and the surface area determines the volume to be suppressed. To achieve maximum utilization of membrane surface for ion exchange, volume to surface area is minimized with a consequent minimization of the time as required to move an ion from the center of the flow path to the membrane. The mesh should be relatively small to maintain chromatographic efficiency but not so small as to hinder the liquid flow. The ion exchange character of the screen is important as the ion exchange sites provide a faster path for ions to the membrane as already described.

In the embodiments of FIGS. 2 and 3, an electrical potential from a direct current source (not shown) is applied between electrodes 42 and 44 from any suitable source. This embodiment is referred to as the electrodialytic mode in contrast to the membrane suppression mode without the application of a potential. The electrodes are formed of highly conductive material which is inert to the solutions being passed through the membrane suppressor. Platinum is a preferred form of electrode for this purpose.

In one mode of operation of the suppressor device 17, effluent from chromatographic column 10 is directed through the effluent flow channel bounded on both sides by ion-exchange membranes 34 and 36 partitioning the regenerant from the effluent. The regenerant flows through the regenerant channels The membrane is preferentially permeable to ions of the same charge as the exchangeable ions of the membrane and resists permeation of ions of opposite charge. The exchangeable ions of the membrane are in the ion form necessary to convert the developing reagent of the eluent to a weakly ionized form. For maximum capacity, the regenerant flow is countercurrent to the effluent flow. The effluent from chromatographic column 10 is passed through the effluent flow channel and contacts both membranes. The membranes are simultaneously contacted on their outer sides with the regenerant flowing in the opposite direction through the regenerant flow channel so that the membrane forms a permselective partition between the regenerant and the effluent. Ions extracted from the effluent at the active ion-exchange sites of the membranes are diffused through the membranes and are exchanged with ions of the regenerant, and thus diffused ultimately into the regenerant. Application of a potential across the electrodes increases the mobility of the ions across the membrane. The resolved ionic species in the effluent leaving the suppressor device are detected, as with a conductivity detector.

FIG. 4 schematically illustrates the electrodialytic mode of operation of the present invention for a particular system, using a sandwich suppressor with screens in the effluent and regenerant channels, and applying an electrical potential between spaced electrodes. The system illustrated is for anion analysis and includes sodium hydroxide as the electrolyte of the effluent to be converted into weakly ionized form ($H_2O$) and dilute sulfuric acid as the regenerant. The ion-exchange membrane sheets allow the positively charged sodium and hydrogen ions to permeate across the membrane together. A suitable ion-exchange membrane for this purpose is a sulphonated polyethylene sheet. Hydroxide and sulfate ions tend not to permeate the membrane sheet because of Donnan Exclusion forces. Thus, the sodium hydroxide stream is converted to deionized water and the sodium ions permeate the membrane sheet and are dispersed in the regenerant as $NaHSO_4$ and $Na_2SO$ and thus ultimately routed to waste through the regenerant outlet lines. Applying a potential across electrodes 42 and 44 increases the kinetics of ion flow across the membrane and thereby increase capacity and, thus, the suppression efficiency of the suppressor device.

In the illustrated embodiment, the sodium ions of the electrolyte in the effluent channel diffuse across the membrane into regenerant channel under the influence of the negative electrode. The hydrogen ions flow from the regenerant channel adjacent the positive electrode across membrane 36 into the effluent flow channel to form water with hydroxide ions therein. Some hydrogen ions which are not used in this manner continue their flow to the regenerant compartment adjacent to the negative electrode 42 at which some of the hydrogen ions are converted to hydrogen gas. The sodium ions, being attracted to the negative electrode, are more rapidly removed from the effluent channel leading to a substantial increase in the capacity of the membrane device.

Bridging means, illustrated as effluent screen 32, and regenerant screens 41 and 43, substantially increase the capacity of the suppressor device to remove ions from the effluent stream. The threads of the screen preferably extend substantially across the effluent flow channel transverse to flow to contact both membranes. In the illustrated device, the effluent screen extends the distance between membranes 34 and 36. This may be accomplished effectively by forming the effluent screen integral with the effluent gasket wall and dimensioning the spacing between the two membrane sheets to be approximately equal to the screen thickness. The gaskets and membranes are relatively flexible and compressible. Thus, by applying appropriate pressure to the rigid support blocks, this distance between the membranes may be adjusted to the desired extent.

The functionalized screens include exchangeable ions of the same charge as those of the membranes. In this manner, the screen provides a direct site-to-site contact between the membrane walls for the ions to be diffused through the membranes. It has been found that the capacity of the system is significantly increased by the use of such functionalized screen in the effluent flow channel. The capacity is still further increased by using the same types of screens in the regenerant flow channel.

Referring again to FIG. 3, the regenerant flow channels may include neutral screens rather than functionalized screens, although this system does not have as much dynamic suppression capacity. The advantage of such unfunctionalized screens is that they provide turbulence in the regenerant flow channel to increase the mixing efficiency. However, if desired, such screens may also be eliminated.

The potential to be applied to the electrodes in the above system may be relatively low due to the presence of the functionalized bridging means in the effluent channel. Thus, capacity is substantially improved with a voltage of about 3-9 VDC, preferably about 5 VDC.

Referring to FIG. 5, a similar system to that of FIG. 3 is illustrated with the exception that there are no electrodes. This membrane suppression mode may be constructed either by eliminating the electrodes or by not applying the potential to existing electrodes. In the membrane suppression mode, the hydrogen ions from both regenerant channels pass through membranes 34 and 36 into the effluent channel with the sodium ions diffusing out of the effluent channel into both regenerant channels. The aforementioned discussion regarding the screens in the effluent and regenerant channels is applicable here. The dynamic suppression capacity of this system is substantially improved by the use of the functionalized screens.

While the above sandwich suppressor embodiment includes a central effluent flow channel separated by two membranes from two coextensive regenerant flow channels, the system is also applicable to the use of a single regenerant flow channel separated from the effluent flow channel by a single membrane.

Referring to FIGS. 6-8, another embodiment of suppressor means 70 is illustrated using a different form of bridging means and using a single regenerant flow channel. Suppressor means 70 includes upper rigid support block 72 with effluent flow channel wall 73 and lower support block 74 with regenerant flow channel wall 75, separated by an ion-exchange membrane 76 of the type described above.

The effluent flows into the suppressor device through effluent inlet 78, fitting 80 and flows along effluent flow channel defined by wall 73 through fittings 82 and out effluent outlet line 84. Similarly, regenerant solution flows from inlet line 86 through fittings 88 across the regenerant flow channel defined by wall 75, out fitting 90 and through regenerant outlet 92 to waste. The device of FIGS. 6-8 is used in the overall system of FIG. 1 in place of the device of FIGS. 3-5.

The particular bridging means of this embodiment is significantly different from that of the screen. Walls 73 and 75 are each textured to provide spaced projections which define a convoluted path for the flow of liquid through the respective flow channels. Referring to the regenerant flow channel, an expanded view of such projections is illustrated in FIG. 7.

One suitable texturing technique is as follows: The 2-dimensional geometric pattern that forms the 3-dimensional convoluted path is computer-generated artwork. This artwork is photographically reduced to the desired dimensions of the texturing required for good chromatographic performance. The background (white area between the black markings of the geometric pattern) is chemically etched into a magnesium block using photosensitive resists of the type commonly used in the circuit-board industry. The etched block is incorporated into a larger block so that a silicone rubber mold can be made which is the negative of the etched block. A textured epoxy block (a positive of the artwork) is made from the rubber mold.

The textured epoxy surface may be functionalized with ion-exchange sites in the same way as the aforementioned membranes.

Referring to FIG. 6-8, the continuous portion of walls 73 and 75 are depressed below the external perimeter wall surfaces 73b and 75b, respectively. When the support blocks 72 and 74 are pressed towards each other, projections 75a (and the analogous projections 73a, not shown), continuously extend substantially the entire distance across the respective flow channels and, preferably, contact membrane 76 on opposite sides of the membrane. In the illustrated embodiment, the projections are in the form of truncated cones. Other types of projections (e.g. cylinders or cubes) may also be employed so long as they provide a convoluted path for the liquid and extend adjacent to the membrane opposite the support wall and, preferably, contact the membrane. The projections preferably form an array of Pascal triangles with the triangular point facing the flow path. Walls 73 and 75 may be formed of the same materials as the screens described above and may be functionalized in the same manner. The projections when functionalized serve the same function as the screens in that they provide a direct site-to-site path for the ions to be transported across membrane 76. Unfunctionalized, the projections provide turbulence.

The liquid flows through the channels formed by the spacing among the projections. The dimensions of the projections and spacing is selected to provide the desired frequency of contacts with the flowing ions to increase their mobility across the membrane and to create sufficient turbulence for increased mixing efficiency.

Suitable eluent solutions for anion ion chromatography include alkali hydroxides, such as sodium hydroxide, alkali carbonates and bicarbonates, such as sodium carbonate, alkali borates, such as sodium borate, combinations of the above, and the eluent systems of the aforementioned patents.

Suitable eluent solutions for cation ion chromatography include mineral acids such as nitric acid, hydrochloric acid, amines such as m-phenylenediamine.2 HCl and combinations thereof and the eluent systems of the aforementioned patents.

Suitable regenerant solutions in the membrane suppression mode for anion ion chromatography include strong organic acids such as sulfosalicylic acid, mineral acids such as sulfuric acid, and combinations thereof and all regenerant solutions previously mentioned in patent literature. In the electrodialytic mode suitable regenerants include those of the membrane suppression mode or water. Water may be used when a suitable voltage is applied to overcome the initially high resistance and effect electrolysis. The electrolysis of water produces hydrogen ion and hydroxide ion, the hydrogen ion being available for suppression of the eluent.

Suitable regenerant solutions in the membrane suppression mode for cation analysis include alkali and alkaline earth and organic amine hydroxides and carbonates such as potassium hydroxide, barium hydroxide, tetramethylammonium hydroxide, potassium carbonate, combinations thereof, and regenerants mentioned in the aforementioned patents. In the electrodialytic mode, the same regenerants and also water may be used.

Referring to FIG. 9, a sandwich suppressor device is illustrated which uses a combination of a textured wall bridging means in both regenerant channels and a screen bridging means in the effluent channel. The suppressor means 100 includes an upper rigid support block 102 with a texturized regenerant flow channel wall 104 and a lower support block 106 with a texturized regenerant flow channel wall 108, both of the same type described with respect to the embodiment of FIGS. 6–8. Ion exchange membranes 110 and 112, of the same type as membranes 42 and 44 of FIGS. 2 and 3, are disposed adjacent to regenerant channel walls 104 and 108, respectively. Sandwiched between membranes 110 and 112 is an effluent gasket 114 defining an effluent flow channel in which is disposed an effluent screen 116, of the type described with respect to the gasket 30 and screen 32 of FIGS. 2 and 3. Also included are regenerant and eluent inlets and outlets (not shown) and clamping means (not shown) compress the support blocks toward each other.

Referring to FIGS. 9 and 10 a continuous electrode plate 118 is formed on the flat or support surface of textured walls 104 and 108 from which the projections 120 extend. Such projections are preferably charged in the manner set forth above for optimum capacity, but may be neutral, if desired. Electrode connections 122 are connected to electrode plates 118, as by welding. The electrode plates may be formed by techniques known in the semiconductor industry. For example, the electrolyte may be disposed in a thin layer in the valleys of the texturized block. Such layer is thin enough to avoid covering a major portion of the projections. Suitable electrolytes includes gold, nickel and platinum, although the latter is preferred.

Considerable experimental work on this system illustrates the following effects of charged parameters upon capacity:

(1) the use of two regenerant chambers rather than one results in a substantial (e.g. 10 or more fold) increase in capacity.

(2) a 45% orientation of weave results in a significant increase in capacity compared to a 90° orientation.

(3) functionalizing the effluent screen or regenerant screens (e.g. to 2 meq/g) results in many-fold increase in capacity.

(4) applying a voltage results in large increases in capacity.

The invention encompasses variations in the above system. For example, other forms of continuous bridging means may be employed Also, the system may be operated with variations on the disclosed functionalized or unfunctionalized bridging means and membranes, and with respect to the presence or absence of an electric potential.

In order to illustrate the present invention, the following examples of its practice are provided.

EXAMPLE 1

In this example, a cation-exchange screen is formed for use as the bridging means illustrated and the suppressor device of FIGS. 2–5. Such bridging means is useful for the analysis of anions by ion chromatography. The base screen is of a polyethylene monofilament type supplied by Tetko, Inc. Such screen is immersed in a solution of 30% styrene w/w in methylene chloride solvent. Grafting occurs by irradiation with gamma rays at a dose of 10,000 rads/hour for about 48–120 hours at 80°–90° F. under nitrogen atmosphere. The screen is then soaked in 10% w/w chlorosulfonic acid in methylene chloride for 4 hours at about 40° C. The screen is then immersed in 1M KOH at 55° C. for 30 minutes.

EXAMPLE 2

In this example, an anion-exchange screen is produced A polyethylene screen of the same type as Example 1 is immersed in 30% vinylbenzylchloride w/w in methylene chloride solvent. Grafting occurs by irradiation with gamma rays at a dose of 10,000 rads/hour for about 100–200 hours at 80°–90° F. under nitrogen atmosphere. The screen is heated under reflux in a solution of 20% trimethylamine w/w in methylene chloride for 24–56 hours.

EXAMPLE 3

In this example, a system of the general type illustrated in FIG. 1 is used with a suppressor device of the general type illustrated in FIG. 2 but without the application of an electrical potential. The device is characterized by dynamic suppression capacity of 300 $\mu$Eq/min. to suppress a chromatographic eluent of 0.1 M NaOH to a background conductivity of 10 $\mu$S/cm. A mixture of condensed phosphates with valence of $-3$ to greater than $-6$ are separated.

The specific characteristics of the suppressor are as follows:
(1) two regenerant flow channels as illustrated in FIG. 2;
(2) a screen capacity of 2 meq/g;
(3) an eluent gasket of dimension 1 cm wide $\times$ 13.4 cm. long (volume 37 $\mu$l), oriented 90° to flow;
(4) regenerant gaskets 1.0 cm. wide $\times$ 10.8 cm. long (volume 27 $\mu$l);
(5) eluent: 0.1 N NaOH, at a flow rate of 2 ml/min.;
(6) regenerant: 0.030 N $H_2SO_4$ at a flow rate of 10 ml./per min;
(7) membranes: cation exchange type supplied by RAI Research Corporation under the designation R1010.

The detector was a conductivity detector 30 $\mu$S/cm fsd, background conductivity 10 $\mu$S/cm.

The results of the test are illustrated on the chromatogram of FIG. 11. This system which had been considered to be impractical due to the relatively concentrated eluents required and the limited dynamic suppression capacity of existing suppressors.

EXAMPLE 4

In this example, the procedure of Example 3 is followed except for the orientation of the weave using the gasketed screens for the effluent and regenerant flow channels. A suppression of 340 $\mu$Eq/min. of hydroxide per device is achieved. A polyethylene screen, (260 μm mesh square weave, 44% open area) is grafted according to Example 1. (The term mesh means the size of the screen opening.) The final ion exchange capacity was 2 meq/g. Rectangles are cut from the screen diagonal to the weave, 2.5 cm × 18 cm. For each gasket two rectangles of Parafilm (American Can Company, Greenwich, Conn.) are cut with the appropriate dimensions of the flow chamber also cut out. The screen is sandwiched between the parafilm gaskets, and the stack is pressed to approximately 5000 psi at ambient temperature.

EXAMPLE 5

In this example, a textured block is used on the effluent chamber side of a two channel suppressor device. The block is formed of an aliphatic amine-cured epoxy resin and is neutral (i.e. non-functional). It includes spaced cones arranged in Pascal triangles at 45° to liquid flow. The textured surface has the following dimensions:

| | |
|---|---|
| Center-to-center cones | 0.017 inch |
| diameter cone | 0.006 inch |
| Total volume measured | 20 μl |
| width × length of textured surface | 1.0 cm × 13.0 cm, |

The device includes a fluorocarbon membrane RAI R1010 and a cation exchange functionalized regeneration screen 1 meg/g capacity, of the type described in Example 1. The device dynamic capacity is 5 μeq/min. It would be substantially greater if the cones were functionalized.

EXAMPLE 6

This example illustrates the use of a sandwich suppressor device to test suppression capacity without separation in comparison to the far improved capacity with the preferred device of Example 7. The component of the device are as follows:

| | |
|---|---|
| Effluent screen (gasketed neutral, vertical square weave) | 1.0 cm wide × 13.4 cm long 110 m mesh |
| Membrane: | Polyethylene cation exchange (type R5010) |
| Regenerant screens (gasketed neutral, vertical square weave) | 1.0 cm wide × 10.8 cm long 260 m mesh |
| Eluent solution: | NaOH |
| Regenerant solution: | 50 mM Sulfosalicylic Acid flow rate (15 ml/min) |

The system capacity is 0.1 μEq/min. With an applied voltage of 4.7 VDC and 1.8 amp, the capacity is 0.8 μEq/min.

EXAMPLE 7

This example illustrates a particularly effective sandwich suppressor in the electrodialytic mode using an NaOH eluent. The effluent screen was of the type set forth in Example 6 except that the weave was oriented 4520 to flow, the mesh size was 180 μm and the screen was functionalized at 2 meq/g. The membrane was cation exchange (R.1010). The regenerant screens were of the same type as the effluent screens but with a 410 μm mesh size.

The regenerant solution was 15 mM $H_2SO_4$, at a flow rate of 10 ml/min. The applied voltage was 4.7 VDC, at 1.8 amps.

The capacity was 340 μEq/g without applied voltage and 520 μEq/g with applied voltage.

EXAMPLE 8

In this example, a suppressor was used with one effluent chamber separated from one regenerant chamber by a single membrane and with charged screens in each chamber. The effluent screen was characterized by 2 meq/g capacity, 1.0 cm width × 13.4 cm length, square weave at 45° orientation, and 260 μm mesh. The eluent solution was NaOH. The membrane was of the same type as Example 7. The regenerant screen had a 2 meq/g capacity, 1.0 cm width × 10.8 cm length, square weave at 45° orientation, and 410 μm mesh size. The regenerant solution was 15 mM $H_2SO_4$ (15 ml/min flow rate).

The capacity was 45 μEq.min.

EXAMPLE 9

In this example, the system of Example 7 was used except that deionized water was used as the regenerant solution and a potential of 5.5 VDC (1.6A) was applied. The capacity was 400 μEq/min.

What is claimed is:

1. Apparatus for ion analysis comprising an eluent reservoir, chromatographic separating means in communication with said eluent reservoir for receiving eluent therefrom, said chromatographic separating means comprising a separating medium adapted to separate ionic species of a sample eluted therethrough using eluent comprising an electrolyte in solution, suppressor means for treating effluent eluted from said chromatographic separating means, said suppressor means including at least on regenerant compartment means and at least one effluent compartment means, an ion exchange membrane sheet partitioning said regenerant compartment means and effluent compartment means and defining therewith a regenerant flow channel and an effluent compartment means flow channel, respectively, said regenerant including a wall opposed to and extending coextensively with said ion exchange membrane sheet, said effluent compartment means including a wall opposed to and extending extensively with said ion exchange membrane sheet, said ion exchange membrane sheet being preferentially permeable to ions of one charge only, positive or negative, and including exchangeable ions of said one charge, bridging means disposed in said effluent flow channel comprising structure including portions extending substantially across the effluent flow channel, said structure defining continuous convoluted liquid flow-through passages in said effluent flow channel along the length of said bridging means, the external surfaces of said structure including ion exchange sites with exchangeable ions of the same charge as the exchangeable ions of said ion exchange membrane sheet, said bridging means being non-integral with said ion exchange membrane sheets, and detector means suitable for detecting resolved ionic species and communicating with said effluent flow channel to receive the treated effluent therefrom.

2. The apparatus of claim 1 in which said structure comprises a screen.

3. The apparatus of claim 2 in which said screen comprises a woven fiber fabric.

4. The apparatus of claim 3 in which the fibers of said screen are perpendicular to each other and are oriented approximately 45° to the direction of fluid flow in said effluent flow channel.

5. The apparatus of claim 1 in which said ion exchange membrane sheet is essentially flat.

6. The apparatus of claim 1 in which substantially all of said exchangeable ions of the structure are of the same charge as said membrane exchangeable ions.

7. The apparatus of claim 1 in which another bridging means is disposed in said regenerant flow channel with exchangeable ions of the same charge as the exchangeable ions of said ion exchange membrane sheet.

8. The apparatus of claim 1 in which said bridging means comprises spaced projections on said effluent compartment means wall extending towards said ion exchange membrane sheet.

9. The apparatus of claim 1 in which said ion exchange membrane sheet is in the ion form necessary to convert electrolyte present in the eluent to a weakly ionized form.

10. The apparatus of claim 1 further comprising a second membrane sheet of the same type and charge as said one ion exchange membrane sheet, said one ion exchange membrane sheet and second membrane sheet defining therebetween said effluent flow channel, a second regenerant compartment means, including a wall opposed to and extending coextensively with said second membrane sheet and defining therewith a second regenerant flow channel disposed on the opposite side of said membrane sheet from said effluent flow channel.

11. The apparatus of claim 10 further comprising first and second spaced electrode means in electrical communication with said regenerant flow channel and second regenerant flow channel, respectively.

12. Suppressor means suitable for treating the effluent from apparatus for separating ionic species in a chromatographic separating medium, said suppressor means including at least one regenerant compartment means and at least one effluent compartment means, an ion exchange membrane sheet partitioning said regenerant compartment means and effluent compartment means and defining therewith a regenerant flow channel and an effluent flow channel, respectively, said regenerant compartment means and effluent compartment means each including walls opposed to and extending coextensively with said ion exchange membrane sheet, said ion exchange membrane sheet being preferentially permeable to ions of one charge only, positive or negative, and including exchangeable ions of said one charge, bridging means disposed in said effluent flow channel and in said regenerant flow channel, said bridging means comprising structure including portions extending substantially across the effluent flow channel and regenerant flow channel, said structure defining continuous convoluted liquid flow passages along the length of said bridging means, the external surfaces of said structure including ion exchange sites consisting essentially of exchangeable ions of the same charge as the exchangeable ions of said ion exchange membrane sheet, said bridging means being non-integral with said ion exchange membrane sheet.

13. The apparatus of claim 12 in which said structure comprises a screen.

14. The apparatus of claim 13 in which said screen comprises a woven fiber fabric.

15. The apparatus of claim 12 in which said bridging means comprises spaced projections on said effluent compartment means wall extending towards said ion exchange membrane sheet.

16. A method of ion analysis comprising eluting a sample containing ions to be quantitated through a separating medium effective to separate ions in the presence of an eluent comprising an electrolyte in solution, thereafter flowing the effluent eluting from the separating medium through the effluent flow channel separated by at least one ion exchange membrane sheet from at least one regenerant flow channel, with bridging means disposed in said effluent flow channel comprising structure including portions extending substantially the entire distance across said effluent flow channel transverse to liquid flow, the exterior surfaces of said structure including ion exchange sites with exchangeable ions of the same charge as the exchangeable ions of said ion exchange membrane sheet, said one membrane sheet being permeable to ions of the same charge as the exchangeable ions of said one membrane sheet and being resistant to permeation therethrough of ions of the opposite charge, and simultaneously flowing regenerant through said regenerant flow channel, said one membrane sheet forming a permselective partition between the regenerant and effluent, said structure forming ion exchange bridges between said one ion exchange membrane sheet and areas of said effluent flow channel remote from said one ion exchange membrane sheet, whereby ions passing along said structure in said regenerant flow channel are extracted from the effluent at the active ion-exchange sites of the one ion exchange membrane sheet are diffused through the one ion exchange membrane sheet and are exchanged with ions of said regenerant, and are thus ultimately diffused into said regenerant flow channel, and detecting resolved ionic species contained in the effluent from said suppressor means.

17. The method of claim 16 in which an electric potential is passed between said effluent flow channel and said one regenerant flow channel transverse to liquid flow to assist diffusion of ions through the membrane.

18. The method of claim 16 in which said bridging means is also disposed in said one regenerant channel.

19. The method of claim 16 in which a second ion-exchange membrane sheet defines said effluent channel with said first ion exchange membrane sheet and regenerant liquid also is directed through a second regenerant channel in contact with said second ion exchange membrane sheet.

20. The method of claim 19 in which an electrical potential is applied between said first regenerant flow channel and second regenerant flow channel across said effluent channel to assist diffusion of ions through said one and second membrane.

21. The apparatus of claim 1 excluding means for passing an electrical potential between said effluent flow channel and said one regenerant flow channel.

22. The method of claim 17 in which no electrical potential is passed between said effluent flow channel and said one regenerant flow channel.

* * * * *

UNITED STATES PATENT AND TRADEMARK OFFICE
CERTIFICATE OF CORRECTION

PATENT NO. : 4,999,098

DATED : March 12, 1991

INVENTOR(S) : Christopher Pohl, et al.

It is certified that error appears in the above-identified patent and that said Letters Patent is hereby corrected as shown below:

Column 14, line 38, delete "on" and insert --one--.

Column 14, line 43, delete "compartment means".

Column 14, line 44, following "regenerant", insert --compartment means--.

Signed and Sealed this

Twenty-second Day of September, 1992

Attest:

DOUGLAS B. COMER

Attesting Officer

Acting Commissioner of Patents and Trademarks